United States Patent [19]

Guthrie

[11] 4,456,685

[45] Jun. 26, 1984

[54] MICROORGANISMS IMMOBILIZED WITH HYDROLYSIS RESISTANT POLYURETHANE FOAM

[75] Inventor: James L. Guthrie, Ashton, Md.

[73] Assignee: W. R. Grace & Co., New York, N.Y.

[21] Appl. No.: 410,373

[22] Filed: Aug. 23, 1982

[51] Int. Cl.$^3$ ............... C12P 13/20; C12N 11/08; C12N 11/04

[52] U.S. Cl. ................................ 435/109; 435/180; 435/182

[58] Field of Search .............. 435/109, 174, 177, 180, 435/182; 521/137, 905

[56] References Cited

U.S. PATENT DOCUMENTS

| | | | |
|---|---|---|---|
| 3,929,574 | 12/1975 | Wood et al. | 435/180 X |
| 4,160,076 | 7/1979 | Guthrie et al. | 521/905 X |
| 4,312,946 | 1/1982 | Wood et al. | 435/182 |
| 4,342,834 | 8/1982 | Wood et al. | 435/182 |
| 4,377,645 | 3/1983 | Guthrie et al. | 521/137 |
| 4,384,050 | 5/1983 | Guthrie | 521/137 |
| 4,384,051 | 5/1983 | Guthrie | 521/137 |

OTHER PUBLICATIONS

Fusee et al., Immobilization of *Escherichia coli* Cells Containing Aspartase Activity with Polyurethane and Its Application for L-Aspartic Acid Production, Applied and Environmental Microbiology, vol. 42, No. 4, 1981 (pp. 672–676).

*Primary Examiner*—David M. Naff
*Attorney, Agent, or Firm*—Richard P. Plunkett; William W. McDowell, Jr.

[57] ABSTRACT

Foams having aspartase-producing microorganisms bound to the foam are made from polyurethane prepolymers which are capped with polyisocyanates, including diisocyanates, derived from methylene-bis (phenyl isocyanate) which is commonly known as MDI. These MDI based foams are hydrolysis resistant as compared to the previously used TDI based foams. The foams can be used to produce L-aspartic acid under high pH conditions.

19 Claims, No Drawings

MICROORGANISMS IMMOBILIZED WITH HYDROLYSIS RESISTANT POLYURETHANE FOAM

BACKGROUND OF THE INVENTION

1. Field of the Invention

This invention relates to an insoluble, hydrolysis resistant polymer foam support onto which microorganisms can be bound.

2. Description of Previously Published and Related Art

It is known to produce aspartic acid by the action of microorganisms which enzymatically convert ammonium fumarate to aspartic acid, and to bind the microorganisms to a porous foamed polyurethane substrate. See U.S. patent application Ser. No. 187,938 filed Sept. 17, 1980 now abandoned, and the article "Immobilization of Escherichia coli Cells Containing Aspartase Activity with Polyurethane and Its Application for L-Aspartic Acid Production" by M. C. Fusee et al in *Applied and Environmental Microbiology*, Vol. 42, No. 4 (October 1981) pg. 672–676. However, the polyurethanes used in the process described in the article were derived from the toluenediisocyanates (TDI) and, therefore, contained urethane linkages which were susceptible to alkaline hydrolysis in the strongly alkaline reaction medium. After about 2 weeks the hydrolysis can cause collapse of the foam support bed.

3. Objects of the Invention

It is an object of this invention to obtain a range of hydrolysis resistant polyurethane polymer foams which can be used to support microorganisms.

It is a further object of this invention to produce L-aspartic acid under high pH conditions with microorganisms bound to a series of hydrolysis resistant polyurethane polymer foams. These and further objects will become apparent as the description of the invention proceeds.

SUMMARY OF THE INVENTION

A series of polymers has been made which are capable of binding microorganisms while simultaneously forming a foamed support which has greatly improved resistance to hydrolysis. The polymers are made from MDI capped prepolymers instead of from TDI capped prepolymers. That is, a water insoluble, hydrolysis resistant, hydrophilic polyether polyurea polyurethane foam having aspartase-producing microorganisms bound to the foam is prepared by reacting under foaming conditions an aqueous mixture containing a culture of aspartase-producing microorganisms and a hydrophilic polyether polyurethane prepolymer, said foam having a weight ratio of polyurea polyurethane polymer to microorganisms in the foam ranging from about 2 to about 4, a weight ratio of prepolymer to water from about 2 to about 0.5 and said prepolymer having an isocyanate functionality in excess of 2 but not greater than 8 with at least 50 mole % of the alkylene oxide units in the polyether segments of the polyurethane being ethylene oxide and obtained by reacting a polyoxyalkylene diol, a diphenylmethane diisocyanate-containing isocyanate product with a functionality of greater than 2.0 comprising a mixture of diphenylmethane diisocyanate and isocyanate containing derivatives of diphenylmethane diisocyanate and a polyol crosslinking agent having 3 or 4 hydroxyl equivalents per mole.

The polymers of this invention can be broadly described as being derived from an ethyleneoxy-based diol such as CARBOWAX ® 1000, a crosslinker such as a polyol having 3 or 4 hydroxyl equivalents per mole such as trimethylolpropane, and any of the polyisocyanates, including diisocyanates, derived from methylene-bis (phenyl isocyanate) commonly known as MDI.

The polymer used in this invention, as opposed to those used in similar applications in the past, does not have hydrolytically unstable linkages and, therefore, lasts much longer under the alkaline conditions of the aspartic acid process.

The flexible foams used according to the present invention are generally water-absorbing and they are made from an isocyanate capped prepolymer by using an MDI derived isocyanate as the sole isocyanate. The prepolymers can be made in two modes. In one mode, described herein as the high MDI mode, the weight of the MDI is at least 50% of the total weight of the MDI, diol and crosslinker present in making the prepolymer. In the other mode, described herein as the low MDI mode, the weight of the MDI is less than 50% by weight of the MDI, diol and crosslinker present in making the prepolymer.

The resulting foams in the high MDI mode are made from prepolymers derived from a poly(oxy $C_{2-4}$ alkylene) diol having at least 50% by weight oxyethylene groups, a diphenylmethane diisocyanate-containing isocyanate product having a functionality greater than 2.0 comprising a mixture of MDI and isocyanate containing derivatives of MDI, and a monomeric polyol crosslinking agent having a hydroxy functionality of 3 or 4. These prepolymers are further described in U.S. Application Ser. No. 314,537 filed Oct. 26, 1981, now U.S. Pat. No. 4,377,645 the disclosure of which is incorporated herein by reference. This prepolymer can react with water in the absence of a catalyst to produce a durable polyurethane foam having many of the characteristics of a cellulose sponge. These foams are white in color.

The preferred components for the high MDI mode prepolymer include a diol having greater than 80% by weight of oxyethylene groups such as Carbowax 1000, trimethylolpropane (TMOP) as the crosslinking agent and as the isocyanate Isonate 143L, which is a methylene-bis(phenyl isocyanate), hereinafter MDI, based isocyanate product of Upjohn Polymer Chemicals having a functionality of approximately 2.1.

In the preferred formulation for the high MDI mode prepolymer Carbowax, a poly(oxyethylene) diol product of Union Carbide, is used to impart the water-absorbing property to provide strength to the foam product through its action as a crosslinking agent. It is important to have the molar ratio of the diol (such as Carbowax) to the monomeric polyol crosslinking agent (such as TMOP) be approximately in the range of 4:1 to 8:1 and preferably about 6:1. Similarly, the ratio of isocyanate equivalents to hydroxyl equivalents in the prepolymer should be in the range of about 3–4:1 and more preferably in tne range of 3.3–3.7:1.

The isocyanate containing product should be more than 50% by weight of the total prepolymer and it should have a functionality greater than 2.0. This would exclude pure MDI which has a functionality of only 2.0 as the only isocyanate. The use of Isonate 143L as the preferred isocyanate source is desirable because it contains dimer, trimer, and carbodiimide components which increase the functionality to a level of greater than 2.0 and which are believed to contribute to the storage stability of the prepolymer and to the strength and dimensional stability of the foam.

The prepolymers in the low MDI mode can be made in two embodiments. One embodiment, hereafter Embodiment A, uses a monomeric polyol crosslinker while the other embodiment, hereafter Embodiment B, uses a polymeric polyol crosslinker. In Embodiment A the resulting foams are made from a prepolymer having at least one poly(oxy $C_{2-4}$ alkylene) diol having a molecular weight of at least about 1100 and having at least 50% by weight oxyethylene groups such as a Carbowax made by Union Carbide, a monomeric polyol crosslinker having 3 or 4 hydroxyl equivalents per mole such as the triol trimethylolpropane and a methylene-bis (phenyl isocyanate), hereinafter MDI, based isocyanate product having a functionality greater than 2.0 such as Isonate 143-L made by Upjohn Polymer Chemicals which has a functionality of approximately 2.1 and which is made of a mixture of MDI and isocyanate containing derivatives of MDI. These prepolymers are further described in U.S. patent application Ser. No. 314, 554 filed Oct. 26, 1981, now U.S. Pat. No. 4,384,050 the disclosure of which is incorporated herein by reference.

In Embodiment B of the low MDI mode the foams are made from a prepolymer having at least one poly-(oxy $C_{2-4}$ alkylene) containing diol with a relatively low molecular weight of less than 2000 and having at least 50% by weight of oxyethylene groups and preferably at least 80% by weight such as a Carbowax 1000 made by Union Carbide; a polymeric poly(oxy $C_{2-4}$ alkylene) polyol crosslinker having 3 or 4 hydroxyl equivalents per mole with a relatively high molecular weight on the order of at least 500 such as the triol TEP 990, a poly-(oxyethylene) triol of approximately 900 molecular weight from Union Carbide or POLY G76-120, an oxyethylene capped poly(oxypropylene) triol of approximately 1400 molecular weight from Olin; and a methylene-bis (phenyl isocyanate), hereinafter MDI, based isocyanate product having a functionality of greater than 2.0 made of a mixture of MDI and isocyanate containing derivatives of MDI such as Isonate 143-L made by Upjohn Polymer Chemicals which has a functionality of approximately 2.1. These prepolymers are further described in U.S. patent application Ser. No. 314,555 filed Oct. 26, 1981, now U.S. Pat. No. 4,384,051 the disclosure of which is incorporated herein by reference.

One of the key features of these prepolymer formulations in the low MDI mode is restricting the amount of the isocyanate such as Isonate 143-L so that it is less than 50% and typically 38-46% of the weight of the prepolymer in Embodiment A and 37-48% of the weight of the prepolymer in Embodiment B. The requirement for the isocyanate component is reduced in Embodiment A by increasing the average molecular weight of a diol component so it is greater than 1100. When using trimethylolpropane as the monomeric crosslinking agent, the preferred diol molecular weight levels are at 1200-1400 and the diol contains at least 80% by weight of oxyethylene groups. The diol used in a preferred embodiment is a mixture of two diols having different molecular weights. For example one diol can have a molecular weight of 1000 while the other can have a molecular weight of 1450. In Embodiment B the requirement for the isocyanate component is reduced by increasing the average molecular weight of the polymeric polyol crosslinking component so it is greater than 500. When using Carbowax 1000 as the diol which has a molecular weight of about 1000, the preferred polymeric polyol crosslinking agent is Poly G176-120 which is a triol with a molecular weight of about 1400.

The actual content of free MDI can be adjusted up or down in this isocyanate containing product so long as the functionality remains greater than 2.0. For example, additional pure MDI could be added.

DESCRIPTION OF SPECIFIC EMBODIMENTS

Aspartase producing microorganisms which are immobilized by the present MDI based polyurethanes are disclosed in U.S. Patent application Ser. No. 187,938 filed Sept. 17, 1980 by W. E. Swann and M. C. Fusee and the disclosure of this application is incorporated herein by reference.

The diol used in making the high MDI mole prepolymer which is used herein is a poly(oxy $C_{2-4}$ alkylene) diol having at least 50% by weight oxyethylene groups and preferably at least 50% by weight oxyethylene groups and preferably at least 80% by weight oxyethylene groups. Thus when the diol contains oxypropylene or oxybutylene or mixtures thereof, there must also be present this minimum amount of oxyethylene. The preferred diol has at least 80% by weight of oxyethylene groups and is a hydrophilic poly(oxyethylene) diol diol made by Union Carbide under the product name Carbowax. When using Isonate 143L as the sole isocyanate source it is preferred to use Carbowax at a molecular weight of about 1000. Other Carbowax formulations having a molecular weight from 600 to 1100 can be used, but the most preferred form has a molecular weight of 950 to 1050. It is this range of products which is produced when making the commercial grade of Carbowax 1000. If a lower molecular weight form than about 600 is used the resulting sponge made from the prepolymer will lose its hydrophilic nature because any sponge formulation would then require a larger amount of relatively hydrophobic Isonate. Similarly, if a higher molecular weight form of Carbowax than 1100 is used, the resulting sponge will lose its crosslink density and much of its dimensional stability and stiffness.

To provide crosslinking strength to the final foam product to be made from the high MDI mode prepolymer, a relatively short, low molecular weight monomeric polyol is added having 3 or 4 hydroxyl equivalents per mole. Examples are trimethylolethane, trimethylolpropane, glycerol, triethanolamine, pentaerythritol or mixtures thereof. The preferred polyol is trimethylolpropane, TMOP, which has the formula

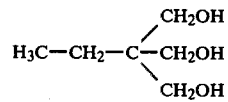

In making the high MDI mode prepolymer it is also desirable to control the ratio of the diol such as Carbowax to the shorter cross-linking polyol. In general the molar ratio should be in the range of about 4:1 to 8:1 with the preferred ratio being about 6:1. If the ratio is too low such that there is too much polyol, then the resulting sponge made from the prepolymer will lose its hydrophilic character and the foam also will have a poorer foam structure. On the other hand if the ratio is increased such that there is less polyol such as TMOP, then weak, flabby foams are obtained which are characterized by fine cells and partially closed cells. The molar ratios which are expressed for these two materials define the relative number of hydroxyl equivalents present from each material. Thus, at a ratio of 6 moles of the preferred diol Carbowax to 1 mole of the preferred polyol TMOP, the Carbowax contributes 12 equivalents of hydroxyl to 3 equivalents from the TMOP.

The Carbowax 1000 has an equivalent weight of 500 per hydroxyl group while TMOP with a molecular weight of 134 has an equivalent weight of 45 per hydroxyl group since the Isonate 143L is used to combine with the hydroxyl groups, the amount of Isonate required will be very sensitive to an amount of TMOP and thus the amount of TMOP is relatively carefully controlled.

The ratio of isocyanate to hydroxyl groups in the reactants should be in the range of 3-4 or more preferably from about 3.3 to 3.7. When the high MDI mode prepolymer is made, one isocyanate group of the polyisocyanate component reacts with a hydroxyl group to leave the remaining isocyanate group unreacted. These free isocyanate groups on the prepolymer then react with water to form polyurea linkages with simultaneous increase in molecular weight and the release of $CO_2$ which aids in forming the foamed product.

The isocyanate containing product should comprise more than 50% by weight of the prepolymer to provide the stiffness required for the foamed product.

When reacting the components to form the high MDI mode prepolymer, it has been helpful to measure the isocyanate level by titration after the reaction has taken place for about one hour. From this reading and subsequent titrations one can determine the additional reaction time required to reduce the isocyanate level down to about the level which is the theoretical point at which all of the hydroxyl groups will have reacted with the isocyanate. If the reaction is permitted to continue for too much further so the isocyanate level is further reduced, then the prepolymer viscosity increases, making it more difficult to subsequently mix the prepolymer with water. Over reacting the prepolymer components will also cause the foam density to increase as well as to decrease the water absorptive property of the resulting foam.

For the low MDI mode the isocyanate component can be advantageously reduced in Embodiment A where the MDI system contains a poly(oxy $C_{2-4}$ alkylene) diol and TMOP, for example, as the monomeric crosslinking agent by increasing the average molecular weight of the poly (oxy $C_{2-4}$ alkylene) diol component to a molecular weight value of greater than 1100. These diols preferably have at least 80% by weight of ethyleneoxy groups. The resulting flexible foams retain their physical properties even when subjected to steam in an autoclave at 120° C. for 5 hours and the foams have a significant decrease in their swell property as compared to TDI foams. TDI based hydrophilic foams swell more than 100% by volume when wet while the present foams swell only 30-60% when wet in Embodiment A.

For the low MDI mode in Embodiment B the isocyanate component can be advantageously reduced where the MDI system uses relatively low molecular weight diols having a molecular weight of less than 2000 by increasing the molecular weight of the polyol crosslinking agent. Instead of using TMOP with a molecular weight of 134, higher molecular weight poly(oxy $C_{2-4}$ alkylene) triols or tetrols are employed which have molecular weights on the order of 500-2000. A preferred example is Poly G176-120 which is a triol with a molecular weight of about 1400. The resulting flexible foams retain their physical properties even when subjected to steam in an autoclave at 120° C. for 5 hours and the foams have a significant decrease in their swell property as compared to TDI foams. TDI based hydrophilic foams swell more than 100% by volume when wet while the present foams swell only from about 30 to 75% when wet in Embodiment B.

The reduced percentage of the isocyanate such as Isonate 143-L in both Embodiments A and B allows the resulting foams to be flexible and resilient, compared to the foams having an Isonate 143-L content of greater than 50% which are semi-rigid and not resilient. Increases in the molecular weights of the diol allows for a decrease in the required amount of Isonate 143-L to such an extent that the ratio of isocyanate functional groups to the hydroxyl functional groups (known as the isocyanate index) can be reduced from 3.5/1 to about 3/1, a change which contributes to the flexibility of the foam product. Although flexibility is best characterized by the flexural modulus, the more readily available tensile modulus at 1% elongation has been used as an approximate classification of these foams into soft and flexible (modulus under 20 psi), firm but flexible (modulus between 20 and 40 psi), and semi-rigid or rigid (modulus above 40 psi).

The preferred isocyanate containing product having a functionality greater than 2.0 for all of the prepolymer compositions is a mixture of diphenylmethane diisocyanate, abbreviated MDI, and isocyanate containing derivatives of MDI. One commercial product meeting this requirement is Isonate 143L which is produced by reacting MDI to form a carbodiimide and this material in turn then reacts to form a tri-functional cycloadduct. The mixture of MDI, the carbodiimide and the cycloadduct are in equilibrium. The mixture contains a major amount of pure diphenylmlethane diisocyanate and minor amounts of carbodiimides and trifunctional cycloadducts of diphenylmethane diisocyanate. A mixture of the A and B components below constitute the 143L system.

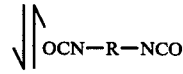
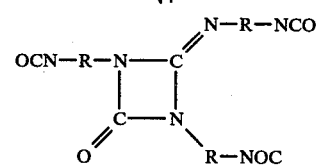
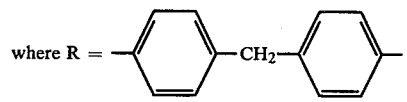
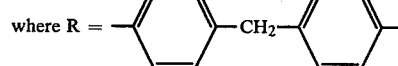

As used herein the term derivatives of diphenylmethane diisocyanate means products that have been made from MDI as a starting material. It would include adducts, dimers and trimers. It would not include materials such as polymethylene polyphenylisocyanates which are not made from MDI.

The prepolymer technology for making foams requires mixing with approximately an equal volume of water. This requires the prepolymer to be hydrophilic and it is the reason that at least some poly(oxyethylene) containing diol must be used in making the prepolymer made from the Isonate 143-L. The desirable viscosity for good mixing and foaming with water is in the range of about 10,000-35,000 cp at 25° C., and preferably about 20,000 cp. Both the viscosity and the hydrophilicity of the prepolymers are controlled by the proper choice of polyol type and molecular weight. The prepolymers must not thicken significantly during storage. It has been found that there will be sufficient storage stability if the viscosity does not rise above 100,000 cp (measured at 25° C.) after accelerated storage testing for two weeks at 80° C.

For a flexible foam to be useful in most applications, it should have a tensile strength of at least 20 psi, a foam density of about 2-6 lb/cu. ft., and an elongation at failure of at least 100% with higher values being preferred. In one example in Embodiment A an elongation at failure of 200% has been obtained while in an example in Embodiment B an elongation at failure of 250% has been obtained The diol used in the low MDI mode prepolymers is a poly(oxy $C_{2-4}$ alkylene) diol containing at least 50% by weight of oxyethylene groups. Thus when the diol contains oxypropylene or oxybutylene or mixtures thereof, there must be also present this minimum amount of oxyethylene. The preferred diols in Embodiment A have at least 80% by weight of oxyethylene groups.

In one of the preferred embodiments of Embodiment A, it has been found satisfactory to use as the diol, a mixture of Carbowax 1000 and Carbowax 1450 manufactured by Union Carbide, although it is within the scope of this embodiment to use any combination of the more preferred poly(oxyethylene) diols with a number average molecular weight of 1000-2000, but preferably in the range of 1200-1400. In these instances the average of the molecular weights of all the diols will be of about at least 1100. By using a blend of these two diols in about equal molar amounts the resulting foams advantageously have low volume swell and low density.

Although it is within the scope of Embodiment A to use any monomeric polyol as the crosslinking agent, the more preferred are those polyol crosslinking agents having 3 or 4 hydroxyl equivalents per mole. These include trimethylolpropane, trimethylolethane, glycerol, triethanolamine, pentaerythritol, or mixtures of these polyols. The most preferred is trimethylolpropane, TMOP, which has the formula

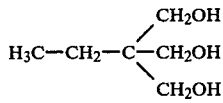

For Embodiment B it has been found satisfactory in the preferred embodiments to use as the diols, Carbowax 1000 or Carbowax 1450 manufactured by Union Carbide, although it is within the scope of the embodiment to use any poly(oxyethylene) diol with a number average molecular weight of 1000-2000, but preferably in the range of 1000-1500.

Although it is within the scope of Embodiment B to use any polymeric polyol as the crosslinking agent, the more preferred are those polymeric poly(oxy $C_{2-4}$ alkylene) polyol crosslinking agents having 3 or 4 hydroxyl equivalents per mole and having a number average molecular weight of at least 500 or mixtures of these polymeric polyols. The most preferred is Poly G76-120 which is a oxyethylene capped poly(oxypropylene) triol of approximately 1400 molecular weight. The oxyethylene moiety here is believed to contain blocks of oxyethylene units attached to a central polyoxypropylene nucleus. It is contemplated that the polyol crosslinker could also consist of a random copolymer of these units.

The density and physical properties of the foams of Embodiments A and B appear to be sensitive to the polyol content. If it is desirable to have a foam with a lower density, but which is firm and less rubbery then the amount of the polyol is increased. Similarly, if it is desirable to have higher density and more elasticity, then the amount of polyol is decreased. The operable amount of polyol crosslinking agent having a hydroxy functionality of 3 or 4 is such that 2% to 35% of the hydroxyl content of the diol and polyol mixture comes from the polyol. The preferred range for a good flexible foam is 10% to 30% hydroxyl from the polyol. In Embodiment B the polyol is a polymeric polyol and generally a relatively small amount of the polymeric polyol is used to keep the prepolymer fluid. When the amount of polyol crosslinking agent is expressed with respect to the amount of diol present, the diol and polyol crosslinking agents are present in Embodiment A in a mole ratio of about 4:1 to 8:1 and in Embodiment B when the amount of polymeric polyol crosslinking agent is expressed with respect to the more plentiful amount of the diol present, the diol and polyol crosslinking agents are present in a mole ratio of about 30:1 to 8:1.

In Embodiment A Carbowax 1000 has an equivalent weight of 500 per hydroxyl group while TMOP with a molecular weight of 134 has an equivalent weight of 45 per hydroxyl group. Since the Isonate 143L is used to combine with the hydroxyl groups, the amount of the isocyanate required will be very sensitive to the amount of TMOP and thus the amount of TMOP is relatively carefully controlled.

In Embodiment B, if the molecular weight of the polyol is too high, then the hydroxyl concentration is so low that it takes too long for the starting materials to react. On the other hand, if the molecular weight is too low and low molecular weight diols are employed, then larger amounts of isocyanate are required and stiff foams are produced.

In Embodiment B Carbowax 1000 has an equivalent weight of 500 per hydroxyl group while Poly G76-120 with a molecular weight of 1400 has an equivalent weight of 467 per hydroxyl group. Since the Isonate 143L is used to combine with the hydroxyl groups, the amount of the isocyanate required will be very sensitive to the amount of Poly G76-120 and thus the amount of Poly G76-120 is relatively carefully controlled.

The operable amount of Isonate 143-L in both Embodiments A and B is such that the isocyanate index is 2.5-3.5, but preferably 2.8 to 3.2 and with very good results at 3.1. Higher ratios allow lower polymer viscosity, lower foam density and less swelling, but they also add cost and reduce softness and elongation. The reaction mechanism and the need to measure the isocyanate level by titration when forming the prepolymer are the same as discussed earlier concerning the high MDI mode.

Surfactants are chosen to give a foam with a good appearance that has the correct cell size, shape and lack of collapse or splits. Surfactants which are known to be useful in polyurethane foams may be employed here. Examples of preferred surfactants are the block copolymers of oxyethylene and oxypropylene such as the Pluronic Polyol surfactants manufactured by BASF Wyandotte Corp. of Wyandotte, Mich. A preferred surfactant is Pluronic L-62.

In making the polyurethane foam the preferred procedure is to add about an equal amount of the aqueous suspension to the prepolymer mixture and to then mix the two together. The composition of the aqueous suspension can be also expressed on the basis of 100 parts of prepolymer resin. Thus, 100 parts of water per 100 parts of resin is written 100 phr water. The ratio of the amount of the prepolymer mixture to the aqueous suspension can vary over a wide range. However, if the amount of the aqueous suspension is too large, then the strength of the resulting foam drops. On the other hand if the amount of the aqueous suspension is decreased too much, then it will not be possible to add enough cells which are supplied via the aqueous suspension.

The preferred method of foaming the prepolymer is to heat the aqueous suspension, for example, a 2% solution of Pluronic L-62 surfactant, as well as the prepolymer, to a temperature of approximately 35° C. These are poured or pumped together in a ratio of about 100 parts by weight of aqueous suspension to about 80 parts by weight of the prepolymer and stirred immediately for up to 30 seconds by a mechanical stirrer such as a blade attached to a drill motor. This length of time allows complete mixing but does not allow an appreciable degree of chemical reaction to occur. This mixture is poured immediately into a mold, where the rising and curing of the foam product takes place.

The process for preparing L-aspartic acid involves contacting a substrate comprising fumarate ion with an MDI-containing foam according to the present invention. The substrate is preferably at a pH of from 8 to 10 and the temperature of the substrate is preferably from 15° C. to 60° C. The substrate preferably contains ammonium fumarate and it can also contain additional magnesium ions. The L-aspartic acid producing process can be carried out on a continuous basis or on a batch basis.

TEST PROCEDURES

The Clorox Test

This test is a simplified method of testing the resistance of foams to hydrolytic degradation in a strongly alkaline medium. The test procedure involves making a foam without any microorganisms by mixing equal volumes of a liquid polymer and a 2% aqueous solution of Pluronic L-62 at 35° C. Then a small foam cube (approximately 150 mg) was cut to fit loosely into a 20 ml screw-cap vial. A concentrated aqueous sodium hypochlorite solution sold under the tradename Clorox is added to the vial. Vials which contained the foam cube and the Clorox solution are rocked at room temperature on a vial rocker in such a manner that the contents move back and forth about 20 times per minute. The time for the foam to dissolve or to break up into fine pieces is measured.

The Swelling Test

This test is a measure of the dimensional stability of the foam. It measures the amount of swelling from the dry state to the wet state. The test procedure involves making a foam without any microorganisms by mixing equal volumes of a liquid polymer and a 2% aqueous solution of Pluronic L-62 at 35° C.

The foam is cut into a rectangular block of about $3 \times 5 \times 1$ inches and the final dimensions are accurately measured. The foam is immersed in water until it is completely saturated. The excess water is squeezed out and the foam is remeasured. The volume is calculated wet and dry. The results are reported as a percent increase in swell from the original dry volume. A low degree of swelling is generally desirable.

The Autoclave Test

This test is also a measure of the hydrolytic stability of the foam. The test procedure involves making a foam without any microorganisms by mixing equal volumes of a liquid polymer and a 2% aqueous solution of Pluronic L-62 at 35° C. The foam sample is placed in a steam autoclave at 120° C. for 5 hours. If the loss in the compression set value is less than 30%, the foam has survived and it is given an "ok" rating.

Having described the basic aspects of our invention, the following examples are given to illustrate specific embodiments thereof.

PREPARATORY EXAMPLE 1

(Comparison)

In this example a TDI containing prepolymer is made for comparison.

A prepolymer was prepared by admixing 2 molar equivalents of Carbowax 1000, polyethylene glycol having an average molecular weight of 1,000 made by Union Carbide and one molar equivalent of trimethylolpropane (TMOP). The admixture was dried at 100° C.–110° C. under a pressure of 5–15 Torr to remove water. The resulting dried mixture was slowly added over a period of about one hour to a vessel containing 6.65 molar equivalents of toluene diisocyanate (TDI) while stirring the TDI and polyol mixture. The temperature was maintained at 60° C. The mixture was maintained at 60° C. with stirring for three additional hours. The final reaction mixture contained a 5% molar deficiency of TDI.

PREPARATORY EXAMPLE 2

This example illustrates the preparation of a prepolymer for use according to the present invention in the high MDI mode.

A mixture of Carbowax 1000 (412 g, 0.4 mole) and trimethylolpropane (9.05 g, 0.0675 mole) were dried by heating for 2 hours at 70° C. under a reduced pressure of 2 Torr. To the dried polyol mixture was added 507.5 g (3.55 equivalents of isocyanate) of Isonate® 143-L, an MDI-based isocyanate product of the Upjohn Company having a functionality of approximately 2.1. The temperature was maintained at 70° C. for 2½ hours, after which time the isocyanate content of the product prepolymer was found to be 2.72 milliequivalents per gram.

PREPARATORY EXAMPLE 3

This example shows the production of a low MDI mode prepolymer of Embodiment A by the use of a combination of two different poly(oxyethylene) diols that produce a prepolymer which will make a softer, finer and more dense foam structure than the foam made from the prepolymer of Preparatory Example 2.

The procedure of Preparatory Example 2 was followed using 348 g (0.35 mole) of Carbowax 1000, 498 g (0.35 mole) of Carbowax 1450, 12.2 (0.09 mole) of trimethylolpropane, and 729 g (5.10 equivalents of isocyanate) of Isonate 143-L. The product prepolymer had an isocyanate content of 2.18 milliequivalents per gram and viscosity of 23,000 centipoises.

PREPARATORY EXAMPLE 4

This example shows the production of a low MDI mode prepolymer of Embodiment A by the use of a different combination of diols. By using a very small amount of triol in combination with a diol of low molecular weight (600) a prepolymer is obtained which produces a strong foam with relatively low density and high porosity which will facilitate the flow of reagents through the resulting foam.

The procedure of Preparatory Example 2 was followed using 122 g. (0.20 mole) Carbowax 600, 263 g. (0.18 mole) of Carbowax 1450, 3.7 g. (0.03 mole) of trimethylolpropane, and 409 g. (2.86 equivalents of isocyanate) of Isonate 143-L. The product prepolymer had an isocyanate content of 2.48 milliequivalents per gram and viscosity of 15,100 cp.

PREPARATORY EXAMPLE 5

This example shows how the prepolymer composition of Preparatory Example 4 can be adjusted with less Carbowax 600 and more trimethylolpropane. The prepolymer obtained will result in a softer and finer foam.

The procedure of Preparatory Example 2 was followed using only 63 g. (0.01 mole) of Carbowax 600, 355 g. (0.24 mole) of Carbowax 1450, 7.8 g. (0.06 mole) of trimethylolpropane, and 374 g. (2.62 equivalents of isocyanate) of Isonate 143-L. The product polymer had an isocyanate content of 2.04 milliequivalents per gram and a viscosity of 36,500 cp.

PREPARATORY EXAMPLE 6

This shows the use of another triol in the prepolymer composition to make a low MDI mode prepolymer of Embodiment B.

The procedure of Preparatory Example 2 was followed using 438 g. (0.3 mole) of Carbowax 1450, 34.5 g. (0.025 mole) of Poly G 76-120 and 370 g. (2.59 equivalents of isocyanate) of Isonate 143-L. The product had an isocyanate content of 2.07 milliequivalents per gram and viscosity of 11,200 cp.

EXAMPLE 1

This example illustrates the production of a foam having bound microorganisms according to the present invention.

The prepolymer of Preparatory Example 2 was reacted with an aqueous part which contained microorganisms with aspartase activity in a manner similar to the procedure described in the article "Immobilization of Escherichia coli Cells Containing Aspartase Activity with Polyurethane and Its Application for L-Aspartic Acid Production" by M. C. Fusee et al in *Applied and Environmental Microbiology*, Vol. 42, No. 4 (October 1981) pg. 672-676. Thus, *E. coli* strain ATCC 11303 was grown under aerobic conditions at 37° C. in a medium containing ammonium fumarate (1.6%), $MgSO_4 \cdot 7H_2O$ (0.05%), $KH_2PO_4$ (0.2%), corn steep liquor (2.0%), and yeast extract (2.0%) (pH adjusted to 7.0). After a 24-hour growth period the cells were harvested by centrifugation (5,000×g, 30 min), and the wet cell paste (80% water) was mixed with the polyurethane prepolymer at ambient temperature (1 part cell paste plus 1 part prepolymer). The water and other isocyanate-reactive groups which reside on the cell surfaces, such as amines, reacted with the isocyanate-capped prepolymer. This reaction caused the formation of a polyurethane polymer which contained entrapped and presumably covalently bound *E. coli* cells containing aspartase activity. The resultant *E. coli* "foam" was ground to an average particle size of 0.5 cm in a Cumberland mill before being assayed for aspartase activity.

The assay for aspartase activity is also described in the Fusee et al article. For immobilized cells, a weight of foam particles containing 1 g of cells was assayed by incubating the particles in a stirred 100-ml solution of 1.0 M ammonium fumarate solution (pH 9.0) containing 1 mM $Mg^{2+}$ at 37° C. for 60 min. Samples were removed at 15-, 30-, and 60-min intervals. The samples were analyzed for loss of fumaric acid and increase of L-malic acid. The difference between the decreased concentration of fumaric acid and the concentration of the L-malic acid produced represents the L-aspartic acid concentration.

Aspartase activity was defined in units per gram (wet weight) of cells, where 1 U is defined as the amount of enzyme given 1/umol of L-aspartic acid per hour at 37° C. under the conditions of the assay. In other words, a unit of activity is defined as micrograms of fumaric acid lost from a standard test solution in one hour at 37° C. The resulting flexible foam was found to have an aspartase activity of 64,655 units per gram of wet cell paste. This indicates that the foam was able to successfully act as an immobilizing agent.

EXAMPLE 2

This example illustrates the stability of foams having bound microorganisms in an alkaline solution of ammonium fumarate.

A control TDI-containing foam was made by mixing together equal weights of the TDI-containing prepolymer of Preparatory Example 1 and the whole cell mass of *Escherichia coli* containing aspartase activity as described in article "Immobilization of *Escherichia coli* Cells Containing Aspartase Activity with Polyurethane and Its Application for L-Aspartic Acid Production" by M. C. Fusee et al in *Applied and Environmental Microbiology*, Vol. 42, No. 4 (October 1981) pg. 672-676.

A foam according to the present invention was made by mixing together equal weights of the prepolymer of Preparatory Example 2 and the same whole cell mass of *E. coli* described above.

Both foams were cut up and then ground into small particles. A mass of both of these foam particles were allowed to stand in a 1.5 M solution of ammonium fumarate at pH 9. The TDI-containing control foam became soft and caused the solution to become turbid and yellow within a few days indicating that it was breaking down. The foam according to the present invention did not soften and the solution remained clear and colorless after two weeks.

EXAMPLE 3

This example illustrates the stability of the foam under reactor conditions.

Foam particles made according to the procedure described in Example 1 were used as the supported catalyst in a continuous bench-scale reactor. The reactor was a jacketed glass column 200 mm in length and having an interior diameter of 16 mm.

The continuous mode recycle reactor operated from a resevoir of solution with a total system volume of 100 cc. The substrate used was fumaric acid adjusted to a pH of 9.0 with ammonium hydroxide. The amount of catalyst particles were 7.5 g based on the wet $E.\ coli$ cells. The catalyst particles were first soaked in 100 ml of substrate at room temperature for one hour. The liquid was drained off and the wet catalyst particles were packed into the column. The catalyst particles were then washed with 100 ml of fresh substrate that was passed through at 6 ml/min., at 37° C. and discarded. Then a 1M substrate was fed to the reactor. To assay for activity, 100 ml of fresh substrate was then immediately recycled through the column at 6 ml/min. and 100 ul samples were removed at various time periods to determine the decrease in fumaric acid concentration. The reactor was run for 20 days during this period the reactor was operated in the presence of either the substrate or product or a mixture of the two at a total combined concentration of 1M substrate plus product. During the test period a fresh substrate was added 4 times. After operating for 20 days, the system was still exhibiting activity without apparent softening or degradation of the foam, and without discoloration of the reactive solutions involved in the process.

EXAMPLE 4

This example illustrates the hydrolytic stability of the foams and their resistance to hydrolytic degradation.

The prepolymers of Preparatory Examples 1-6 were made into foams following the procedure set forth in the Clorox Test. The foams were then evaluated by the Clorox Test, the Swelling Test and the Autoclave Test. The results are set forth in Table 1 below along with the density of the foams.

TABLE 1

| | Foams Made From Prepolymer of Preparatory Example | | | | | |
|---|---|---|---|---|---|---|
| | 1 (TDI Comparison) | 2 | 3 | 4 | 5 | 6 |
| Clorox Test (Minutes) | 7 | 200 | 190 | 120 | 100 | 160 |
| Swelling Test (volume %) | 147 | 5-15 | 37 | 37 | 53 | 45 |
| Autoclave Test | liquified* | ok | ok | ok | ok | ok |
| Density (lb/ft$^3$) | 8.8 | 2.5 | 4.2 | 3.7 | 4.9 | 5.3 |

*The TDI foam liquified in the autoclave.

The TDI containing foam readily broke down in the hydrolytic stability Clorox test, its volume swelled almost 150%, it failed the autoclave test and it had a very high density. All of the foams made from the MDI containing prepolymers had remarkably superior properties.

It is understood that the foregoing detailed description is given merely by way of illustration and that many variations may be made therein without departing from the spirit of this invention.

What is claimed is:

1. A water insoluble, hydrolysis resistant, hydrophilic polyether polyurea polyurethane foam having aspartase-producing microorganisms bound to the foam prepared by reacting under foaming conditions an aqueous mixture containing a culture of aspartase-producing microorganisms and a hydrophilic polyether polyurethane prepolymer, said foam having a weight ratio of polyurea polyurethane polymer to microorganisms in the foam ranging from about 2 to about 4, a weight ratio of prepolymer to water is from about 2 to about 0.5, and said prepolymer having an isocyanate functionality in excess of 2 but not greater than 8 with at least 50 mole % of the alkylene oxide units in the polyether segments of the polyurethane being ethylene oxide, and obtained by reacting a poly(oxy-C$_{2-4}$alkylene) diol having at least about 50% by weight of oxyethylene groups.

a diphenylmethane diisocyanate-containing isocyanate product with a functionality of greater than 2.0 comprising a mixture of diphenylmethane diisocyanate and isocyanate containing derivatives of diphenylmethane diisocyanate, and a polyol cross-linking agent having 3 or 4 hydroxyl equivalents per mole.

2. A foam according to claim 1, wherein said isocyanate product comprises a mixture of a major amount of pure diphenylmethane diisocyanate and minor amounts of carbodiimides and trifunctional cycloadducts of diphenylmethane diisocyanate.

3. A foam according to claim 1, wherein said prepolymer is either (A) a prepolymer derived from
   (a) a poly(oxy C$_{2-4}$ alkylene) diol having at least about 50% by weight of oxyethylene groups and a nominal number average molecular weight of about at least 1100, said diol having nominally two hydroxyl equivalents per mole,
   (b) a diphenylmethane diisocyanate-containing isocyanate product with a functionality of greater than 2.0 comprising a mixture of diphenylmethane diisocyanate and isocyanate containing derivatives of diphenylmethane diisocyanate, and
   (c) a monomeric polyol crosslinking agent having 3 or 4 hydroxyl equivalents per mole,
   said isocyanate containing product comprising less than 50% by weight of the prepolymer,
   said diol and polyol crosslinking agent being present in a mole ratio in the range of about 4:1 to 8:1, and
   the ratio of the isocyanate equivalents to the total hydroxyl equivalents being in the range of about 2.5:1 to 3.5:1;

(B) a prepolymer derived from
   (a) a poly(oxy C$_{2-4}$ alkylene) diol having at least about 50% by weight of oxyethylene groups and a nominal number average molecular weight of about less than 2000, said diol having nominally two hydroxyl equivalents per mole,
   (b) a diphenylmethane diisocyanate-containing isocyanate product with a functionality of greater than 2.0 comprising a mixture of diphenylmethane diisocyanate and isocyanate containing derivatives of diphenylmethane diisocyanate, and
   (c) a polymeric poly(oxy C$_{2-4}$ alkylene) polyol crosslinking agent having 3 or 4 hydroxyl equivalents per mole, and having a number average molecular weight of at least 500
   said isocyanate containing product comprising less than 50% weight of the prepolymer,
   said polymeric polyol crosslinking agent being present so that the hydroxy equivalents constitute 5 to 35 mole % of the total hydroxy equivalents in the diol and polyol, the ratio of the isocyanate equivalents to the total hydroxyl equivalents being in the range of about 2.5:1 to 3.5:1; or (C) a prepolymer derived from
  (a) a poly(oxy $C_{2-4}$ alkylene) diol having at least about 50% by weight of oxyethylene groups and a nominal number average molecular weight of about at most 1100, said diol having nominally two hydroxyl equivalents per mole,
  (b) a diphenylmethane diisocyanate-containing isocyanate product with a functionality of greater than 2.0 comprising a mixture of diphenylmethane diisocyanate and isocyanate containing derivatives of diphenylmethane diisocyanate, and
  (c) a monomeric polyol cross-linking agent having 3 or 4 hydroxyl equivalents per mole, said isocyanate product comprising more than 50% by weight of the prepolymer, said diol and polyol crosslinking agent being present in a mole ratio in the range of 4:1 to 8:1, and the ratio of the isocyanate equivalents to the total hydroxyl equivalents being in the range of 3:1 to 4:1.

4. A foam according to claim 3, wherein the nominal number average molecular weight of the poly(oxy $C_{2-4}$ alkylene) diol in part A is between 1100 and 2000 and the diol has at least 80% by weight of oxyethylene groups and wherein the nominal number average molecular weight of the poly(oxy $C_{2-4}$ alkylene) diol in part B is 600-2000 and the diol has preferably at least 80% by weight of oxyethylene groups.

5. A foam according to claim 4, wherein the nominal number average molecular weight of the poly(oxy $C_{2-4}$ alkylene) diol in part A is between 1200 and 1500 and wherein the nominal number average molecular weight of the poly(oxy $C_{2-4}$ alkylene) diol in part B is between 950 and 1500.

6. A foam according to claim 3, wherein the poly(oxy $C_{2-4}$ alkylene) diol in part A comprises a mixture of at least 2 diols each having a different nominal number average molecular weight.

7. A foam according to claim 6, wherein the poly(oxy $C_{2-4}$ alkylene) diol in part A comprises a mixture of a diol with a molecular weight of about 1000 and a diol of a molecular weight of about 1450.

8. A foam according to claim 3, wherein the polyol crosslinking agent in part A and part C is selected from the group consisting of trimethylolpropane, trimethylolethane, glycerol, triethanolamine, pentaerythritol, and mixtures thereof and wherein the polymeric polyol crosslinking agent in part B is selected from the group consisting of a poly(oxyethylene) triol having a molecular weight of about 900, and an oxyethylene-capped poly(oxypropylene) triol having a molecular weight of about 1400 and mixtures thereof.

9. A foam according to claim 3, wherein the nominal number average molecular weight of the poly(oxy $C_{2-4}$ alkylene) diol in part C is between 600 and 1100 and the diol has at least 80% by weight of oxyethylene groups.

10. A foam according to claim 3, wherein said isocyanate product comprises a mixture of a major amount of pure diphenylmethane diisocyanate and minor amounts of carbodiimides and trifunctional cycloadducts of diphenylmethane diisocyanate.

11. A process for preparing L-aspartic acid wherein a substrate comprising fumarate ion is contacted with the foam according to claim 1.

12. A process as in claim 11, wherein the substrate has a pH of from 8 to 10.

13. A process as in claim 11, wherein the temperature of the substrate is from 15° C. to 60° C.

14. A process as in claim 11, wherein the substrate comprises ammonium fumarate.

15. A process as in claim 11, wherein the substrate comprises magnesium ion.

16. A process as in claim 11, said process carried out on a continuous basis.

17. A process as in claim 11, said process carried out on a batch basis.

18. A process for preparing L-aspartic acid wherein a substrate comprising fumarate ion is contacted with the foam according to claim 2.

19. A process for preparing L-aspartic acid wherein a substrate comprising fumarate ion is contacted with the foam according to claim 3.

* * * * *